United States Patent [19]

Fareed et al.

[11] Patent Number: 4,970,144
[45] Date of Patent: Nov. 13, 1990

[54] PEPTIDE FRAGMENTS OF HUMAN APOLIPOPROTEIN, TYPE-SPECIFIC ANTIBODIES AND METHODS OF USE

[75] Inventors: George Fareed; Arup Sen, both of Los Angeles, Calif.

[73] Assignee: International Genetic Engineering

[21] Appl. No.: 905,584

[22] PCT Filed: Dec. 26, 1985

[86] PCT No.: PCT/US85/02569

§ 371 Date: Sep. 2, 1986

§ 102(e) Date: Sep. 2, 1986

Related U.S. Application Data

[63] Continuation-in-part of Ser. No. 688,040, Dec. 31, 1984, abandoned.

[51] Int. Cl.$^5$ .............. G01N 33/532; G01N 33/543; G01N 33/68; G01N 33/92
[52] U.S. Cl. .............................. 435/5; 437/7; 437/810; 436/518; 436/536; 436/545; 436/546; 436/547; 436/823; 530/327; 530/328; 530/387; 530/807
[58] Field of Search .............. 435/7, 810, 5; 436/547, 436/804, 807, 518, 536, 545, 823; 530/326, 327, 328, 387, 807

[56] References Cited

U.S. PATENT DOCUMENTS

| | | |
|---|---|---|
| 4,126,416 | 11/1978 | Sears . |
| 4,167,467 | 9/1979 | Golias . |
| 4,311,788 | 1/1982 | Heuck . |
| 4,399,217 | 8/1983 | Holmquist . |
| 4,478,744 | 10/1984 | Mezei ............................ 530/329 X |
| 4,493,795 | 1/1985 | Nestor ........................... 530/327 X |
| 4,521,334 | 6/1985 | Beachey . |
| 4,544,500 | 10/1985 | Bittle . |
| 4,554,101 | 11/1985 | Hopp . |

OTHER PUBLICATIONS

Brewer et al., Biochem. Biophys. Res. Comm., 80, 623–630, (1978).
Rall et al., J. Biol. Chem., 257, 4171–4178, (1982).
Brewer et al., J. Biol. Chem., 249, 4975–4984, (1974).
Le Boeuf et al., FEBS LETTERS, 170, 105–108, (1984).
Tikkdnen et al., Arteriosclerosis, 4, 138–146, (1984).
Tago, Inc., "Apolipoprotein B and Apolipoprotein A–1 Immunoassays", (Sales Brochure), (1983).
Ventrex Laboratories, Inc., RIA for Apoliproprotein A–1, (Sales Brochure), (1984).
Hopp, T. P. et al., Proc. Natl. Acad. Sci., 78(6), 3824–3828, (1981).
Lerner, R. A., Nature, 299, 592–596, (1982).

Primary Examiner—Sidney Marantz

[57] ABSTRACT

Peptide fragments of certain apolipoproteins have been found to be both immunogenic and capable of eliciting antibodies with highly apolipoprotein-specific immunoreactivity. These antibodies, in labeled and unlabeled form, as well as the labeled synthetic peptide fragments, are useful in the production of immunodiagnostic procedures and kits for quantitating type-specific apolipoproteins. Both competitive assays and immunometric assays are disclosed.

11 Claims, 8 Drawing Sheets

PEPTIDE DOMAINS OF APO-A$_1$ SHOWING APO-A$_1$ SPECIFICITY (A, B, AND C)

AND SYNTHETIC PEPTIDES PRODUCED THEREFROM (A', B' AND C')

A      Asp-Glu-Pro-Pro-Gln-Ser-Pro-Trp-Asp-Arg-Val-Lys-Asp

A'      NH$_2$-Asp-Glu-Pro-Pro-Gln-Ser-Pro-Trp-Asp-Arg-Val-Lys-Asp-Cys-COOH

B      Arg-Thr-His-Leu-Ala-Pro-Tyr-Ser-Asp-Glu-Leu-Arg-Gln-Arg-Leu

B'      NH$_2$-Arg-Thr-His-Leu-Ala-Pro-Tyr-Ser-Asp-Glu-Leu-Arg-Gln-Arg-Leu-Cys-COOH

C      Val-Lys-Ala-Lys-Val-Gln-Pro-Tyr-Leu-Asp-Asp-Phe

C'      NH$_2$-Val-Lys-Ala-Lys-Val-Gln-Pro-Tyr-Leu-Asp-Asp-Phe-Cys-COOH

PEPTIDE DOMAINS OF APO-A₁ SHOWING APO-A₁ SPECIFICITY (A, B, AND C)
AND SYNTHETIC PEPTIDES PRODUCED THEREFROM (A', B' AND C')

A    Asp-Glu-Pro-Pro-Gln-Ser-Pro-Trp-Asp-Arg-Val-Lys-Asp

A'   NH₂-Asp-Glu-Pro-Pro-Gln-Ser-Pro-Trp-Asp-Arg-Val-Lys-Asp-Cys-COOH

B    Arg-Thr-His-Leu-Ala-Pro-Tyr-Ser-Asp-Glu-Leu-Arg-Gln-Arg-Leu

B'   NH₂-Arg-Thr-His-Leu-Ala-Pro-Tyr-Ser-Asp-Glu-Leu-Arg-Gln-Arg-Leu-Cys-COOH

C    Val-Lys-Ala-Lys-Val-Gln-Pro-Tyr-Leu-Asp-Asp-Phe

C'   NH₂-Val-Lys-Ala-Lys-Val-Gln-Pro-Tyr-Leu-Asp-Asp-Phe-Cys-COOH

*FIG. 1*

A PEPTIDE DOMAIN OF APO-E SHOWING APO-E SPECIFICITY (A)
AND A SYNTHETIC PEPTIDE CORRESPONDING THERETO (A')

A      Ala-Val-Glu-Thr-Glu-Pro-Glu-Pro-Glu-Leu-Arg

A'    $NH_2$-Ala-Val-Glu-Thr-Glu-Pro-Glu-Pro-Glu-Leu-Arg-Cys-COOH

*FIG. 2*

PEPTIDE DOMAINS OF APO-C$_3$ SHOWING APO-C$_3$ SPECIFICITY (A, B, AND C)
AND SYNTHETIC PEPTIDES CORRESPONDING THERETO (A', B', AND C')

A        Asp-Pro-Glu-Val-Arg-Pro-Thr-Ser-Ala-Val

A'        NH$_2$-Asp-Pro-Glu-Val-Arg-Pro-Thr-Ser-Ala-Val-Cys-COOH

B        Leu-Lys-Asp-Tyr-Trp-Ser-Thr-Val-Lys-Asp-Lys-Phe

B'        NH$_2$-Leu-Lys-Asp-Tyr-Trp-Ser-Thr-Val-Lys-Asp-Lys-Phe-Cys-COOH

C        Ser-Glu-Ala-Asp-Ala-Ser-Leu-Leu-Ser-Phe

C'        NH$_2$-Ser-Glu-Ala-Asp-Ala-Ser-Leu-Leu-Ser-Phe-Cys-COOH

*FIG. 3*

PEPTIDE DOMAINS OF APO-B HAVING APO-B SPECIFICITY (A AND B)
AND SYNTHETIC PEPTIDES CORRESPONDING THERETO (A' AND B')

A  Leu-Asp-Phe-Leu-Asn-Ile-Pro-Leu-Arg-Ile-Pro-Pro-Met-Arg

A'  $NH_2$-Leu-Asp-Phe-Leu-Asn-Ile-Pro-Leu-Arg-Ile-Pro-Pro-Met-Arg-Cys-COOH

B  Ala-Lys-Pro-Ser-Val-Ser-Val-Glu-Phe-Val-Thr-Asn

B'  $NH_2$-Ala-Lys-Pro-Ser-Val-Ser-Val-Glu-Phe-Val-Thr-Asn-Cys-COOH

*FIG. 4*

PEPTIDE DOMAINS OF APO-$A_2$ SHOWING APO-$A_2$ SPECIFICITY (A AND B)
AND SYNTHETIC PEPTIDES CORRESPONDING THERETO (A' AND B')

A            Gln-Ala-Lys-Glu-Pro-Cys-Val-Glu-Ser-Leu

A'           $NH_2$-Gln-Ala-Lys-Glu-Pro-Cys-Val-Glu-Ser-Leu-Cys-COOH

B            Glu-Lys-Val-Lys-Ser-Pro-Glu-Leu-Gln-Ala-Glu-Ala-Lys-Ser

B'           $NH_2$-Glu-Lys-Val-Lys-Ser-Pro-Glu-Leu-Gln-Ala-Glu-Ala-Lys-Ser-Cys-COOH

| ApoB | ApoA-1 | ApoC-III | Control | VLDL |
|---|---|---|---|---|
| ● 2 | ● 0.75 | ● 4 | ○ 4 | ● 2 |
| ● 1.6 | ● .38 | ● 2 | ○ 2 | ● 1 |
| ● 1.2 | ● .19 | ● 1 | ○ 1 | ○ .5 |
| ○ 1 Stds | ○ 1 Stds | ○ 1 | ○ 1 | ○ 1 |
| ● .4 Stds/Apo | ● .38 Stds/Apo | ● 2 | ○ 2 | ○ 1 |

PEPTIDE FRAGMENTS OF HUMAN APOLIPOPROTEIN, TYPE-SPECIFIC ANTIBODIES AND METHODS OF USE

CROSS REFERENCE TO RELATED APPLICATION

The following application is a continuation-in-part of U.S. patent application Ser. No. 688,040, filed Dec. 31, 1984, and abandoned as of Jan. 10, 1987.

TECHNICAL FIELD

This invention is directed to the discovery that certain apolipoprotein (ALP) peptide fragments (or domains or moieties) are immunogenically active and can be used to produce type-specific antibodies that recognize ALP's. The resulting fragments and ALP type-specific antibodies are useful in another aspect of the invention, assay systems for quantitating ALP levels.

BACKGROUND ART

Lipoproteins are aggregates of lipids and protein which circulate in the blood and are the means by which lipids are transported within the body. The lipid portions of these aggregates consist essentially of cholesterol and triglyceride. Serum lipoproteins are classified according to their density. These classes include very low density lipoproteins (VLDL), also known as pre-beta lipoproteins; low density lipoproteins (LDL), also known as beta-lipoproteins; and high density lipoproteins (HDL), also known as alpha-lipoproteins. A fourth class of lipoproteins is chylomicron (CHYLO), stable droplets containing 86% triglyceride fat, 3% cholesterol, 9% phospholipids, and 2% protein. Chylomicrons are found in the intestinal lymphatics and blood during and after meals, and are the form in which absorbed long-chain fats and cholesterol are transported from the intestine.

One of the functions of lipoproteins is to carry water insoluble substances, such as cholesterol and cholesterol esters, for eventual cellular utilization. While all cells require cholesterol for growth, excess accumulation of cholesterol by cells is known to lead to certain diseases, including atherosclerosis. It is now known that the amount of total serum cholesterol can be correlated with the incidence of atherosclerosis. However, since all lipoprotein classes contain varying amounts of cholesterol, total serum cholesterol determination is a complex average of the amount that each lipoprotein class contributes to the total lipoprotein population of the serum.

Recent studies have implicated LDL as the class of lipoproteins responsible for the accumulation of cholesterol in cells, whereas HDL has been shown to be important in the removal of excess cholesterol from cells. Additionally, the correlation of atherosclerosis and the levels of LDL cholesterol is much higher than a similar correlation between atherosclerosis and total serum cholesterol levels. Conversely, there seems to be a negative correlation of atherosclerosis and HDL cholesterol levels. See Goffman, J. W. et al, Circulation, 2: 161–178 (1950); Barr, D. P. et al., Am. J. Med., 11: 480–493 (1951); Nikkala, E., Scand. J. Clin. Lab. Invest. Supplement, 5: 1–101 (1952); Jencks, W. P. et al., J. Clin. Invest., 35: 980–990 (1956), and Miller, G. J. et al., Lancet, 1(7897): 16–19 (1975).

Thus, because the various classes of lipoproteins contain cholesterol and triglyceride in different proportions, determination of only total cholesterol and total triglyceride is not sufficient to differentiate abnormal lipoprotein patterns. Recognition of this fact has led investigators to various procedures designed to determine concentrations of specific lipoproteins rather than just lipids. U.S. Pat. No. 4,126,416 to Sears describes a method for determining the level of LDL cholesterol in blood plasma, the LDL cholesterol being separated from other soluble cholesterol fractions by selectively agglutinating LDL with a plant lectin, followed by detection of the amount of cholesterol associated with the agglutinated LDL.

U.S. Pat. No. 4,167,467 to Golias describes an electrophoresis method for determining the concentration of HDL free cholesterols in body fluids and simultaneously determining the concentration of VLDL and LDL free cholesterols in the fluid sample. The method includes applying a direct current across the fluid medium, applying a developing substrate to the electrophoresed lipoproteins, and quantitatively determining the concentration of each lipoprotein free cholesterol. The method of Golias purports to be an improvement over the prior art in that direct and simultaneous measurement of each lipoprotein free cholesterol fraction is achieved without precipitation of each fraction.

U.S. Pat. No. 4,185,963 to Heuck describes a method for determining lipids in blood serum wherein the VLDL, CHYLO, and HDL are extracted from the serum with a polycation, followed by measuring the lipid content of the LDL in the serum.

U.S. Pat. No. 4,215,993 to Sanders describes a method for isolating HDL from LDL in human serum, followed by quantitative determination of HDL cholesterol. LDLs are precipitated from the serum without the addition of metal ions to the sample. The precipitating reagent lowers the pH of the human serum approximately to the isoelectric point of the LDL through the use of an organic buffer.

U.S. Pat. No. 4,309,188 to Bentzen describes a separation method wherein LDL and HDL are separated on a microcolumn containing a support which has a sulphated polysaccharide covalently bound thereto. Elution with a first pH buffered solution collects the LDL; elution with a second pH buffered solution collects the HDL. Subsequently, LDL/HDL ratios can be determined.

U.S. Pat. No. 4,039,285 to Teipel discloses a single-sample method for determining concentrations of individual lipoprotein classes and lipids in blood by turbidimetric measurement. The ionic strength of the mixture is raised in steps to cause progressive dissolution of each class of complex from that of the highest density lipoprotein to the lowest density lipoprotein. Measurement of the turbidity due to the insoluble complexes present at each step allows the concentration of each lipoprotein class and lipid in the blood sample to be calculated.

Recent epidemiological studies on cardiovascular illness have shown the advantage of determining not only the global amount of serum lipoproteins and distinction according to the group to which these lipoproteins belong, but also, within these groups, according to the type of apolipoprotein (ALP) present, and especially the amount of each ALP present. Apolipoprotein is the protein moiety which binds the lipid moiety to form the holoprotein. At present, a number of types and subtypes of ALP have been identified.

Apolipoprotein A (Apo-A) includes subtypes $A_1$ and $A_2$. Apo-$A_1$ is the major apolipoprotein of HDL and is thought to occupy a surface position on HDL particles, surrounding a neutral lipid core. It is also known that Apo-$A_1$ activates lecithin:cholesterol acyl transferase, the cholesterol-esterifying enzyme of plasma involved in the production of mature circulating HDL. As mentioned above, there is an inverse correlation between plasma HDL levels and development of coronary artery heart disease. See also, Heiss, G. et al., *Circulation*, 62:Suppl. IV, 116 (1980).

The second most abundant apolipoprotein of HDL is Apo-$A_2$. It has been reported that Apo-$A_1$ binds less total HDL lipid than does Apo-$A_2$; however, in an interaction between these apolipoproteins, Apo-$A_2$ increases the binding capacity of Apo-$A_1$. Morrisett et al., "Lipoproteins: Structure and Function," *Annual Review of Biochemistry*, 44: 183, 196-198 (1975).

Highly purified LDL has been shown to contain a single molecule of a very large protein, apolipoprotein B (Apo-B), having a molecular weight estimated to be 250,000 to 500,000 daltons. See Smith, et al., *J. Biol. Chem.*, 247: 3376 (1984) and Milne, R. W. and Marcel, I. L., *FEBS Lett.*, 146: 97 (1982). LDL plays a key role in the transport of cholesterol to the peripheral tissues where it is bound to cellular receptors and ingested by an endocytosis process. LDL is also known to play an important role in the pathological uptake and deposition of cholesterol, with very high concentrations of LDL implicated as the causative agent of some forms of human atherosclerosis. Additionally, moderate elevations of LDL over long periods of time may be an important factor in the development of most human atherosclerosis. See Goffman et al., *Science*, 111: 166 (1951); Goldstein et al., *Metabolism*, 26: 1257 (1977). Apo-B is known to play a number of important roles in triglyceride and cholesterol transport and is required for the formation and secretion of triglyceride-rich lipoproteins from human liver. It is the only protein always found on LDL and contains a site complementary to, and recognized by, the LDL receptor. There is also evidence demonstrating that the presence of a certain allele of pig Apo-B correlates strongly with lipid deposition and plaque formation in pig artery. See Rapacz et al., *Exp. and Mol. Path.*, 27: 429 (1977).

Apolipoprotein C (Apo-C) includes subtypes Apo-$C_1$, Apo-$C_2$, and Apo-$C_3$. Apo-C has been shown to be part of the protein moiety of plasma lipoproteins (Eisenberg, S. et al., *J. Biol. Chem.*, 254: 12603 (1979)). Apo-C, which makes up 40-80% of the total protein of CHYLO and VLDL, is present in plasma HDL, and plays an important role in the regulation of the activity of the enzyme system lipoprotein lipase. Recently, a relationship between the extent of VLDL triglyceride hydrolysis and the content of Apo-C in the lipoprotein has been established, with Apo-C molecules being transferred from VLDL to HDL following abrupt triglyceride hydrolysis, and returning to VLDL when newly secreted particles enter the circulation. Similar observations have been reported during clearance and induction of alimentary chylomicronemia.

One apolipoprotein particularly central to the removal or uptake process for circulating cholesterol-laden lipoproteins is apolipoprotein E (Apo-E). See Mahley, R. W., *Med. Clin. North. Amer.*, 66: 375 (1982). An important function of Apo-E is its mediation of cellular uptake of lipoproteins through specific surface receptors. See Mahley, R. W., *Klin. Wochenscher.*, 61: 225 (1983). Apo-E is known to bind to the low density lipoprotein receptor of fibroblast and various peripheral cells, thereby affecting intracellular cholesterol metabolism. It also binds specifically to a hepatic plasma membrane receptor, the Apo-E receptor, and functions as a prime determinant in chylomicron remnant clearance.

Apolipoprotein E (Apo-E) includes three major iso forms, Apo-$E_2$, Apo-$E_3$, and Apo-$E_4$. Amino acid sequence analysis has demonstrated that the three iso forms differ in their primary structure. Variant forms of Apo-$E_2$ have been described, with all forms of Apo-$E_2$ demonstrating reduced LDL receptor binding activity and reduced Apo-E receptor binding activity. Further, these abnormal forms of Apo-$E_2$ are associated with the genetic abnormality type III hyperlipoproteinemia, which appears to be partly due to the defective clearance of cholesterol-rich remnant lipoproteins (Weisgraber, H. K. et al., *J. Biol. Chem.*, 258: 12341 (1983)). This evidence suggests that Apo-E performs a critical role in cholesterol and lipid metabolism as well.

Based on the recently recognized evidence relating to the interaction of various cellular receptors and ALPs in mediating removal of cholesterol-containing lipoproteins from circulation, efforts have mounted to develop specific assays for ALPs. U.S. Pat. No. 4,399,217 to Holmquist et al. describes a process for the determination of serum lipoproteins by an immunoenzymatic method. Apolipoprotein antibodies are fixed on a support. Serum sample is added, in combination with enzyme-labeled specific apolipoprotein. Elimination of all reagent not fixed on the support, followed by measurement of the enzymatic activity bound to the support, produces an indirect determination of the amount of specific apolipoproteins present in the sample being analyzed in a competitive assay. Thus, the assay requires "type-specific" antibody and specific labeled antigen (apolipoprotein) and a competitive assay system. The "type-specific" antibody is produced by immunizing rabbits with purified apolipoprotein obtained by serum lipoprotein fractions separated by ultracentrifugation on a density gradient. Unfortunately, ultracentrifugation is somewhat deficient with regard to obtaining highly pure apolipoprotein fractions. Accordingly, the "type-specificity" of the resulting antibodies produced by rabbit immunization is deficient as well. Thus, a need has continued to exist for a highly accurate, truly type-specific assay for apolipoproteins and high specificity antibodies for the same.

DISCLOSURE OF THE INVENTION

Recognizing the role that various ALPs play in cholesterol metabolism and the need for an accurate, efficient and inexpensive assay of high ALP specificity, the inventors evaluated known amino acid sequences of various ALPs in an effort to identify regions within the polypeptides which would be both immunogenic and immunospecific. These efforts have culminated in the identification of specific polypeptide moieties (fragments) in the amino acid sequences of each of Apo-$A_1$, Apo-$A_2$, Apo-B, Apo-C and Apo-$E_2$ which are both immunogenic and immunospecific.

The inventors then successfully synthesized the polypeptide fragments, conjugated the fragments with carrier proteins, and produced truly type-specific, non-cross-reactive antibodies by immunization.

Assays, competition and sandwich types, involving detectably labeled antibody, substratum-immobilized antibody, and dectably labeled immunospecific peptides of this invention or purified ALP's have been developed as well.

BRIEF DESCRIPTION OF THE DRAWINGS

FIG. 1 shows three peptide sequences (A, B, and C) which are each specific for Apo-$A_1$ as well as three synthetic peptides used to raise Apo-$A_1$ specific antibodies (A', B', and C').

FIG. 2 shows a peptide sequence which is specific for Apo-$E_2$ as well as a synthetic peptide used to raise Apo-$E_2$ specific antibody ($A^1$).

FIG. 3 shows three peptide sequences (A, B, and C) which are specific for Apo-$C_3$ as well as three synthetic peptides used to raise Apo-$C_3$ specific antibodies (A', B', and C').

FIG. 4 shows two peptide sequences (A and B) which are each specific for Apo-B as well as two synthetic peptides used to raise Apo-B specific antibodies (A' and B').

FIG. 5 shows two peptide sequences (A and B) which are specific for Apo-$A_2$ as well as two synthetic peptides used to raise Apo-$A_2$ specific antibodies (A' and B').

FIG. 7 is a diagram representing immunodot blots obtained from varying amounts of different apolipoproteins spotted onto nitrocellulose filters.

BEST MODE FOR CARRYING OUT THE INVENTION

Figure 6A:
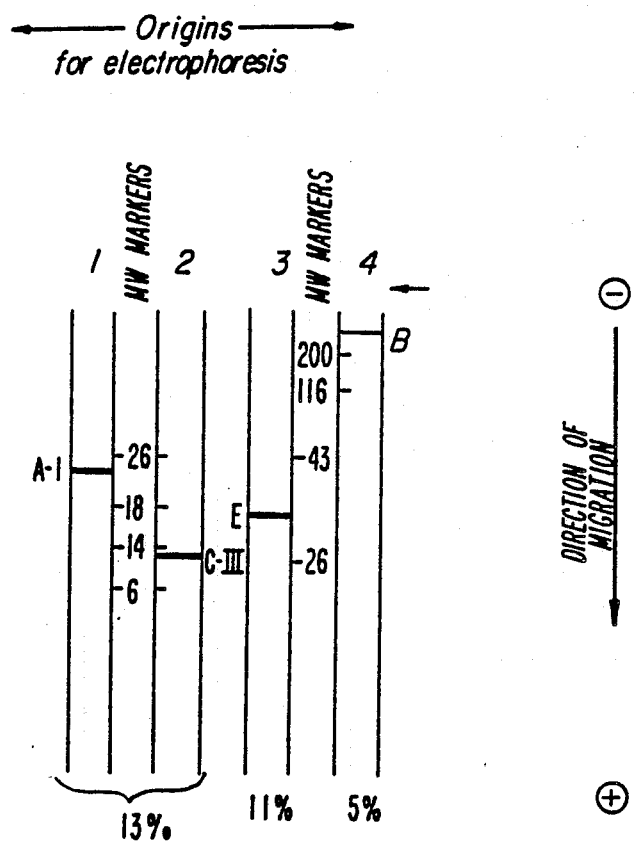
FIG. 6 (A and B) are diagrams of Western Immunoblots obtained from SDS-PAGE gels, utilizing the Specific Protocol IV below.

Peptide moieties (fragments) chosen from the determined amino acid sequences of various apolipoproteins constitute the starting point in the development comprising the present invention. The amino acid sequence for apolipoprotein $A_1$ has been reported in the literature by Brewer, H. B., Jr. et al., *Biochem. Biophys. Res. Commun.*, 80: 623–630 (1978). The amino acid sequence of human Apo-$A_2$ is published in Morrisett et al., "Lipoproteins: Structure and Function," *Annual Review Biochemistry*, 44: 183–207 (1975). Similarly, the complete amino acid sequence for apolipoprotein $E_2$ has been reported by Rall, S. C., Jr., et al., *J. Biol. Chem.*, 257: 4171–4178 (1982). The complete amino acid sequence for apolipoprotein $C_3$ is also known, Brewer, et al., *J. Biol. Chem.*, 249: 4975–4984 (1974). Amino-terminal sequences for certain proteolytic fragments derived from apolipoprotein B are known as well, reported by LeBoeuf, R. C. et al., *FEBS Letters*, 170: 105–108 (1984).

Peptide domains corresponding to various segments within the naturally occurring amino acid sequence are obtained. In one embodiment, the peptide fragments are synthesized by the well known solid phase peptide synthesis described by Merrifield, *J. Am. Chem. Soc.*, 85: 2149 (1962) and Stewart and Young, in *Underlying Solid Phase Peptide Synthesis* (Freeman, San Francisco, 1969), pp. 27–62, incorporated by reference herein. However, it is also possible to obtain the fragment by fragmenting a naturally-occurring amino acid sequence, using, for example, a proteolytic enzyme or a chemical agent.

Thus, the term "peptide fragment," "peptide domain" and "peptide moiety" is meant to include both synthetic and naturally-occurring amino acid sequences representing portions of the natural protein, typically containing 8–20 amino acids in the sequence, more preferably 10–16 amino acids, with 12–15 member oligopeptides representing the preferred chain length. The terms "derivable from a naturally-occurring amino acid sequence" are meant to include both synthetic sequences and sequences obtained by fragmenting naturally-occurring sequences to obtain isolated sequences which do not exist in nature as such. Also, included are oligopeptides that, in addition to the chosen sequence, may contain one or more amino acids that may not be present in the naturally-occurring sequence. This invention also relates to novel polypetides generated by covalent coupling of two or more distinct peptide moieties (fragments) resulting in an immunospecific peptide comprising two or more domains which are non-contiguous in the natural ALP proteins.

Various peptide fragments were evaluated to determine immunogenicity (the property that endows a substance with the capacity to provoke a humoral immune response and the degree to which the substance possesses this property) and immunospecificity (the ability of the antibodies provoked by the immune response to bind to specific lipoprotein or apolipoprotein). The term "apolipoprotein type-specific" is meant to include highly specific immunoreactivity limited to a particular ALP.

Referring to FIG. 1, A, B, and C represent three naturally-occurring amino acid sequences found in Apo-$A_1$. A', B' and C' represent the three peptides which were synthesized and evaluated for their ability to elicit antibody production and represent the actual synthetic peptides which were utilized as the antigenic material. Note that each of the synthesized sequences contains an additional cysteine residue at the carboxy terminus to allow for coupling of carrier protein.

Referring now to FIG. 2, A represents the amino acid sequence for Apo-$E_2$ which was evaluated for immunogenicity and immunospecificity for Apo-$E_2$. Again, the synthesized peptide fragment A' includes a cysteine residue at the carboxy terminus to allow for coupling to a carrier protein.

Referring to FIG. 3, peptide sequences corresponding to A, B, and C were evaluated for immunogenicity and immunospecificity to apolipoprotein $C_3$. Each synthetic peptide includes a cysteine residue at the carboxy terminus to allow for coupling to a carrier protein (A', B' and C').

Referring to FIG. 4, the two sequences A and B represented therein were evaluated for immunogenicity and immunospecificity to apolipoprotein B. The synthetic peptides further corresponding thereto, A' and B' include a cysteine added to each carboxy terminus for coupling to a carrier protein.

Referring to FIG. 5, A and B represent two naturally-occurring amino acid sequences found in Apo-$A_2$, which were evaluated for immunogenicity and immunospecificity for Apo-$A_2$. The synthesized peptide fragments A' and B' include a cysteine residue at the carboxy terminus to allow for coupling to a carrier protein.

Included within the scope of the present invention are those amino acid sequences in the noted fragments which are both immunogenic and immunospecific. Accordingly, the peptide fragments include one or more epitopes, i.e. immunogenic domains (determinants), capable of producing the desired ALP-type specific antibodies and may be the peptide fragment corresponding exactly to the natural sequence or varying to a degree which does not impact on immunogenicity and immunospecificity relevant to their use according to this invention. Included as well are the use of additional amino acid residues added to enhance coupling to carrier protein or amino acid residues added to enhance labelling or to enhance the immunogenicity of the peptide fragments by amnio acid sequences which cause activation of an animal's immune system (immune response capabilities). By the term "labelable residue" is meant to include a residue such as tyrosine which is present in or has been introduced into the desired sequence in order to make possible the affixing of a detectable label, for example, a radioisotope such as $^{125}$I, an enzyme, or a fluorescent tag.

Of particular interest are peptides of the following formula:

(1) $H_2N—X—CO—R^1$ wherein $R^1$ is $Cys—CO—R^2$, OH, OM or $—NR^3R^4$;

M is a pharmaceutically acceptable cation or a lower ($C_1-C_6$) branched or unbranched alkyl group;

$R^2$, $R^3$ and $R^4$ are the same or different and selected from the group consisting of hydrogen and a lower ($C_1-C_6$) branched or unbranched alkyl group; and X is the amino acid sequence or peptide fragment as described above;

(2) the acid addition salts thereof; and (3) the protected or partially protected derivatives thereof.

As is known in the art, the amino acid residues may be in their protected or unprotected form, using appropriate amino or carboxyl protecting groups.

Useful cations M are alkali or alkaline earth metallic cations (i.e., Na, K, Li, ½ Ca, ½ Ba, etc.) or amine cations (i.e., tetraalkylammonium, trialkylammonium, where alkyl can be $C_1-C_{12}$).

The variable length peptides may be in the form of the free amines (on the N-terminus), or acid-addition salts thereof. Common acid addition salts are hydrohalic acid salts, i.e., HBr, HI, or more preferably, HCl.

ELISA titers for all of the synthetic peptide antisera prepared according to the present invention (using 5 ng peptide per well) is greater than 1:1600 and generally greater than 1:12000. ELISA titers for the Apo-$A_1$ antisera using 100 ng per well of native Apo-$A_1$ was greater than 1:12000.

In order to stimulate the production of antibody, the antigenic material (the peptide fragment) may be coupled to a carrier protein such as albumin or keyhole limpet hemocyanin (KLH), utilizing techniques well known and commonly used in the art. Preferably, the carrier protein is KLH, linked to the antigenic material through a cysteine residue.

Additionally, the antigenic material can be admixed with an immunologically inert or active carrier. Carriers which promote or induce immune responses, such as Freund's complete adjuvant, can be utilized.

The preparation of antisera in animals is a well known technique (see, for example, Chard, *Laboratory Techniques In Biochemistry And Molecular Biology*, "An Introduction to Radioimmunoassay and Related Techniques," pages 385–396, North Holland Publishing Company (1978)). The choice of animal is usually determined by a balance between the facilities available, and the likely requirements in terms of volume of the resultant antiserum. A large species such as goat, donkey and horse may be preferred, because of the larger volumes of serum readily obtained. However, it is also possible to use smaller species such as rabbit or guinea pig which often yield high titer antisera. Usually, subcutaneous injection of the antigenic material (the peptide fragment hapten-carrier protein conjugate) are introduced into the immune system of the animal in which antibodies are to be raised. The detection of appropriate antibodies may be carried out by testing the antisera with appropriately labeled tracer-containing molecules. Fractions that bind tracer-containing molecules are then isolated and further purified if necessary. These antibodies may then be utilized in various immunoassays to identify and quantitate specific ALP's. The immunoassays within the scope of the present invention include both competitive assays and immunometric assays.

General competitive binding assay techniques useful for the detection of minute amounts of organic molecules such as hormones, proteins, antibodies, and the like are well known in the art. See Chard, supra. Any of these competitive binding assay techniques can be used for the purposes of the present invention, i.e., quantitating specific ALP. In order to carry out a competitive binding assay, typically a radioimmunoassay (RIA), it is necessary to provide a binding molecule which has affinity for the labelcontaining molecule and for the ALP as well. A small amount of the fluid or tissue sample containing an unknown quantity of ALP is incubated in the presence of the antibody and also a known amount of labeled antibody-specific antigen. The antibody need not necessarily be (although is preferably) generated with the antigenic peptide fragments of the invention. Typically, however, the same synthetic peptide used to generate the antibody and containing additionally a tyrosine residue is radioiodine labeled through the tyrosine residue and comprises the tracer-containing molecule. Once the incubation of the test sample with the antibody and tracer-containing molecule is complete, it is necessary to determine the distribution of the tracer-containing molecule between the free and bound (immunocomplexed) form. Usually, but not always, this requires that the bound fraction be physically separated from the free fraction. For example, the antibody raised against a specific ALP can be bound to a plate. A variety of other techniques may be used for that purpose, each exploiting physical-chemical differences between the tracer-containing molecule in its free and bound form. The generally available methodologies have been described by Yalow, in *Pharmacol. Rev.*, 28: 161 (1973). These techniques include adsorption, precipitation, salting out techniques, organic solvents, electrophoretic separation, and the like. See Chard, supra, pp. 405–422.

Radioactive isotopes which are particularly useful are $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, and $^{152}Eu$.

While radiolabeling represents one embodiment, alternatively, the peptide sequence may also be labeled using fluorescent labels, enzyme labels, free radical labels, avidin-biotin labels, or bacteriophage labels, using techniques known to the art (Chard, supra).

Typical fluorescent labels include fluorescein isothiocyanate, rhodamine, phycoerythrin, phycocyanin, allophycocyanin, o-phthaldehyde, and fluorescamine.

Typical chemiluminescent compounds include luminol, isoluminol, aromatic acridinium esters, imidazoles, acridinium salts, and the oxalate esters. Typical bioluminescent compounds include luciferin, luciferase, and aequorin.

Typical enzymes include alkaline phosphatase, beta-galactosidase, glucose-6-phosphate dehydrogenase, maleate dehydrogenase, glucose oxidase, and peroxidase.

Two principal types of enzyme assays are enzymelinked immunosorbent assay (ELISA) and the homogeneous enzyme immunoassay, also known as enzyme-multiplied immunoassay (EMIT) (Syva Corp.). In the classic ELISA system, separation is achieved by the use of antibodies coupled to a solid phase. The EMIT system depends on deactivation of the enzyme in the tracer-antibody complex; the activity can thus be measured without the need for a separation step.

The ALP type-specific antibodies of the present invention are also useful for use in an immunometric assay, also known as sandwich immunoassay. These immunometric assays include simultaneous sandwich, forward sandwich, and reverse sandwich immunoassays. Each of these terms is well understood by those skilled in the art.

In a forward sandwich immunoassay, a sample is first incubated with a solid phase immunoabsorbent containing antibody against the ALP. Incubation is continued for a period of time sufficient to allow the ALP in the sample to bind to the immobilized antibody in the solid phase. After the first incubation, the solid phase immunoabsorbent is separated from the incubation mixture and washed to remove excess ALP and other interfering substances which also may be present in the sample. Solid phase immunoabsorbent-containing ALP bound to the immobilized antibodies is subsequently incubated for a second time with soluble labeled antibody cross-reactive with a different domain on the ALP. After the second incubation, another wash is performed to remove unbound labeled antibody from the solid phase immunoabsorbent and to remove nonspecifically bound labeled antibody. Labeled antibody bound to the solid phase immunoabsorbent is then detected and the amount of labeled antibody detected serves as a direct measure of the amount of antigen present in the original sample. Alternatively, labeled antibody which is not associated with the immunoabsorbent complex can also be detected, in which case the measure is in inverse proportion to the amount of antigen present in the sample. Forward sandwich assays are described, for example, in U.S. Pat. Nos. 3,867,517; 4,012,294; and 4,376,110.

In a reverse sandwich assay, the sample is initially incubated with labeled antibody, after which the solid phase immunoabsorbent containing immobilized antibody cross-reactive with a different domain on the ALP is added thereto, and a second incubation is carried out. The initial washing step required by a forward sandwich assay is not required, although a wash is performed after the second incubation. Reverse sandwich assays have been described, for example, in U.S. Pat. Nos. 4,098,876 and 4,376,110.

In a simultaneous sandwich assay, the sample, the immunoabsorbent having immobilized antibody thereon and labeled soluble antibody specific to a different domain are incubated simultaneously in one incubation step. The simultaneous assay requires only a single incubation and does not require washing steps. The use of a simultaneous assay is a very useful technique, providing ease of handling, homogeneity, reproducibility, linearity of the assays, and high precision. See U.S. Pat. No. 4,376,110 to David et al., incorporated by reference herein.

In each of the above assays, the sample-containing antigen, solid phase immunoabsorbent with immobilized antibody and labeled soluble antibody are incubated under conditions and for a period of time sufficient to allow antigen to bind to the immobilized antibodies and to the soluble antibodies. In general, it is desirable to provide incubation conditions sufficient to bind as much antigen as possible, since this maximizes the binding of labeled antibody to the solid phase, thereby increasing the signal. Of course, the specific concentrations of labeled and immobilized antibodies, the temperature and time of incubation, as well as other such assay conditions, can be varied, depending upon various factors including the concentration of antigen in the sample, the nature of the sample, an the like. Those skilled in the art will be able to determine operative and optimal assay conditions for each determination by employing routine experimentation.

There are many solid phase immunoabsorbents which have been employed and which can be used in the present invention. Well known immunoabsorbents include beads formed from glass, polystyrene, polypropylene, dextran, nylon, and other material; tubes formed from or coated with such materials, and the like. The immobilized antibodies may be covalently or physically bound to the solid phase immunoabsorbent, by techniques such as covalent bonding via an amide or ester linkage or by absorption.

As in the competitive assays described above, the soluble antibody may be labeled with any detectable label, such as a radiolabel, a fluorescent label, an enzyme label, a free radical label, or a bacteriophage label. Most commonly, the label is a radiolabel or an enzyme label.

As described above, the immunometric assays require two separate and distinct antibodies which are type-specific as regards apolipoprotein. One of these antibodies is bound to the solid phase support while the other is detectably labeled. In essence, the two different antibodies, although ALP type-specific, are cross-reactive with different domains within the antigenic protein. In one embodiment, the two different antibodies may be prepared by using two different synthetic sequences which correspond to different immunogenic and immunospecific segments within the amino acid sequence of the ALP. For example, referring to FIG. 1, both the synthetic peptide A' and synthetic peptide B' have been found to be both immunogenic and immunospecific as regards Apo-A$_1$. The use of antibodies to each synthetic sequence, one bound to a substrate and the other detectably labeled, is useful in the various sandwich assays.

Alternatively, it is also possible to prepare antibodies which are type-specific to the same apolipoprotein, but cross-reactive with different domains by producing the antisera in two different species, for example, in rabbit and in mouse, utilizing the same synthetic peptide sequence.

So-called delayed immunometric assays can also be utilized, as are, for example, described in Chu, U.S. Pat. No. 4,289,747, and Wolters, U.S. Pat. No. 4,343,896.

In addition, the materials for use in the assays of the invention are ideally suited for preparation of a kit. Such a kit may comprise a carrier means being compartmentalized to receive in close confinement one or more container means such as vials, test tubes, and the like. Each of said container means comprises one of the separate elements to be used in the method.

For example, one of said container means may comprise immunoabsorbent-bound antibody. These antibodies may be bound to a separate solid phase immunoabsorbent or directly to the inner walls of a container. A second container may comprise detectably labeled peptide fragment in lyophilized form or in solution.

The carrier may also contain, in addition, a plurality of containers each of which comprises different, predetermined known amounts of antigen or peptide fragments. These latter containers can then be used to prepare a standard curve from which can be interpolated the results obtained from the sample containing the unknown amount of antigen.

GENERAL PROTOCOLS

I. Immunization

Peptides conjugated to KLH have been used to immunize laboratory animals, such as rabbits, in order to generate monospecific antibodies capable of binding to the respective apolipoproteins. In a typical experiment, approximately 100 micrograms (ug) of the particular protein to which antibodies are to be raised is admixed with Freund's complete adjuvant and inoculated into the footpads and at subcutaneous sites in rabbits, ten to fourteen days later a comparable amount of protein admixed with incomplete Freund's adjuvant is inoculated subcutaneously; after an additional ten to fourteen days, the animal is inoculated with an additional 50-100 ug of protein mixed in a ten percent solution of aluminum hydroxide. The animal is subsequently immunized at four week intervals with 50-100 ug of protein.

II. Assays

The specific antibody titers developed against the respective proteins have been measured by (a) an enzyme-linked immunosorbent assay (ELISA) and by (b) the ability of the antibody to immunoprecipitate radiolabeled protein molecules. In a typical ELISA assay, 10-100 nanograms of the test antigen (that is, the particular protein being tested) is bound to a plastic surface by air-drying of a protein solution on the bottoms of wells in microtiter dishes (Falcon Products or Bellco Products). Serial dilutions of test antisera are incubated within the wells, unbound antibodies are removed by washing and the bound antibodies are then incubated with an enzyme-conjugated second antibody preparation directed against the immunoglobulins of the species in which the test antiserum was generated. The amount of enzyme bound in each well is then quantitated by an appropriate color assay. In such testing, sera with high titers of antibody against the test antigen can be diluted several thousand fold and will still show significant color development. It has been found that the storage temperature (room temperature, 4° C., −20° C., and −80° C.) of the serum sample to be tested will result in detection of the same level of apolipoprotein, regardless of temperature.

In the other assay, that is, the radioimmunoprecipitation assay (RIP), the test antigen is labeled with a radioisotope such as $^{125}I$. A fixed quantity of the radiolabeled antigen is then incubated with serial dilutions of the test antisera. The immunocomplexed antigen is precipitated, either using a second antibody directed against the immunoglobulins of the species in which the test serum was generated, or using a fixed *Staphylococcus aureus* bacterial suspension, or using *Staphylococcus aureus* protein A immobilized onto beads. As in the previously noted ELISA procedure, serum with high titers of specific antibody can be diluted several thousand fold and still precipitate significant amounts of the radiolabeled antigen.

In either assay, the specific titers of antibodies in test sera samples are determined by subtracting the values (color or precipitated radioactivity) obtained with serum from nonimmunized animals or from animals immunized with a protein which is unrelated to the test protein. The specificity of the antisera as well as the immunological relatedness of different proteins can be estimated in either assay by examining the relative effects of serum dilutions on the extent of binding of the antigen.

III. Immunoblot Procedures

In a typical immunoblot procedure, proteins are first subjected to a polyacrylamide gel electrophoresis (PAGE) in the presence of a denaturing and a reducing agent. The proteins are then transferred onto a nitrocellulose membrane electrophoretically in a conducting solution containing Tris-HCl, glycine and methanol (or isopropanol). The nonspecific binding sites on the nitrocellulose membrane are blocked using a Tris-NaCl buffer containing bovine serum albumin (3%–5% wt/vol). An appropriate dilution of the specific antiserum in the above buffer is then contacted with the nitrocellulose membrane in order to allow the binding of the antibody molecules to the specific protein. Unbound antibody is washed using a Tris-buffered salt solution supplemented with a nonionic detergent such as Tween 20. The protein band(s) that has (have) bound antibody can then be visualized by (1) colorimetric means using an enzyme-conjugated second antibody directed against the immunoglobulins of the species in which the specific antibody was generated or (2) autoradiography using radiolabeled protein A from *Staphylococcus aureus* to bind to the immunoglobulin molecules that had bound to the specific antigen on the nitrocellulose membrane. This technique of immunoblotting allows one to identify the molecular species being recognized by a specific antibody. Thus, this technique can be applied to establish the type-specificity of an anti-peptide antibody serum by using a mixture of apolipoproteins (such as in plasma or serum) as the test sample.

Once the type-specificity of an antibody preparation has been established, a much simpler approach can be used for quantitating the amount of a specific protein. This method, referred to herein as "immuno dot blot," involves spotting a small volume of an aqueous solution on a nitrocellulose filter, fixing the protein on the nitrocellulose using an acid alcohol mixture such as acetic acid:isopropanol:water (10:20:70 v/v) and then performing the antibody binding technique described above.

In order to obtain low background reactivities in the immuno dot blot method, the serum samples to be tested are first treated by boiling and reduction by adding 0.1% SDS solution with 10 mM dithiothrietol to the serum. This solution is then placed in boiling water for 10 minutes. Upon cooling at room temperature, the sample is then treated with an equal volume of commercially available pansorbin. The sample can then be assayed for APL.

SPECIFIC PROTOCOLS

Protocols for the practice of the present invention:

I. Conjugation of Peptide to Keyhole Limpet Hemocyanin (KLH)

Reaction

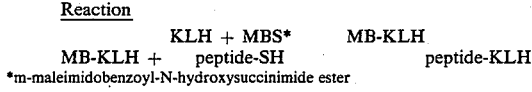

*m-maleimidobenzoyl-N-hydroxysuccinimide ester

Materials

1. KLH, dialyzed against 10mM phosphate buffer (PB), pH 7.2. Adjust to ca. 20 mg/ml before use.
2. Peptide, at ca. 5 mg/ml. Weigh fresh before coupling.
3. MBS.
4. DMF (Dimethyl formamide).
5. PBS (phosphate buffered saline).

Procedure

1. Use glass or other non-plastic tube.
2. To 200 ul of KLH add 55 ul of PB, and slowly add 85 ul of MBS (3 mg MBS/500 ul DMF).
3. Stir 30' at room temperature.
4. Run through Sephadex G-25 column (approx. 15 ml bed volume), prewashed with 50 mM sodium phosphate buffer pH 6.0.
5. Collect approximately 1 ml fraction.
6. Read the absorbance at 280 nm.
7. Pool the peak tubes containing MB-KLH.
8. Add 5 mg peptide in 1 ml PB (+100,000 cpm of $^{125}$I-peptide, if available) to 4 mg of MB-KLH.
9. Adjust pH to 7-7.5 (with NaOH or HCl).
10. Stir at room temperature for 2-4 hours.
11. Dilute into 10 mls total with PBS.
12. Freeze in 0.5 ml aliquots.

II. Rabbit Immunization

First injection—day 1—

Mix peptide-KLH complex (200 ug per rabbit) in a final volume of 1.5 ml PBS, with 1.5 ml incomplete Freund's adjuvant and 3 mg mycobacterium; emulsify. Inject 1.5 ml/rabbit in the footpads, and in a few places along the back subcutaneously.

Second injection—day 14—

Same as for first injection, but omit the mycobacterium.

Third injection—day 21—

Mix peptide-KLH complex (200 ug per rabbit) in a final volume of 1.2 ml PBS containing 10 mg/ml of Al(OH)$_3$. Shake well, inject 1 ml/rabbit (intraperitoneal or subcutaneous).

Routinely, rabbits are bled 7 and 14 days after the third injection (or days 28 and 35 from the beginning).

Boosts are the same as the third injection, in Al(OH)$_3$, and rabbits are bled 7 and 14 days later.

The amount of peptide/rabbits which will induce a good response in the boosts can be cut down to 50 ug KLH (coupled to peptide) per rabbit.

III ELISA PROCEDURE

1. Plate ca. 10 ng to 100 ng of protein in 50 ul of PBS pH 7.4 per well onto a 96 well dish.
2. Incubate overnight in a 37° C. incubator uncovered to dry the wells.
3. Fill the wells with absolute methanol to fix the protein onto the dish.
4. Wash twice with distilled H$_2$O.
5. Block the non-specific binding sites in the wells with 100 ul of 3% BSA/0.05% Tween 20 in phosphate buffered saline (PBS). Incubate in a humidified chamber at 37° C. for 2-4 hrs.
6. Wash the wells with a 0.05% Tween 20 supplemented PBS solution twice and follow with two washes in distilled H$_2$O.
7. Add the desired range of serial dilutions of the test antibody in consecutive wells in the dish (with dilutions made in PBS containing 1% BSA and 0.05% Tween 20).
8. Incubate the dishes in a humidified chamber at 37° C. for 2 hours.
9. Repeat step #6.
10. Add 50 ul of the desired dilution of Goat-Anti-(appropriate species) Peroxidase conjugate to each well and incubate 1 hr at 37° C.
11. Repeat step #6.
12. Add 50 ul of the freshly prepared O-phenylenediamine dihydrochloride (OPD) solution in phosphate-citrate buffer containing 0.01% H$_2$O$_2$ to each well.
13. Let the reaction proceed until the desired color is attained.
14. At the desired time, quench the reaction with 50 ul of 4N H$_2$SO$_4$ in each well.
15. Read the color developed in the wells at 490 nanometers.

IV. WESTERN BLOT PROCEDURE

1. Wash the polyacrylamide gel twice (10 min each) with a buffer containing Tris-HCl (20 mM), Glycine (150 mM), Methanol (20% v/v) at a pH of 8.3.
2. Soak a nitrocellulose paper of the size of the gel in the above buffer.
3. Transfer by conventional technique in a standard electroblot apparatus (i.e., from BioRad, Richmond, California) in the above buffer.
4. Block the nonspecific binding sites by soaking in a blocking buffer, i.e. Buffer B containing 3% BSA and 0.1% NP40.

Buffer B is 10 mM Tris base, 150 mM NaCl, pH 7.4

5. Rinse filters in distilled H$_2$O.
6. Add the appropriate amount of antibody to the blocking buffer to reach the desired dilution. Shake the nitrocellulose filter with this diluted antibody solution for 2-4 hours or overnight at 20°-25° C.
7. Wash extensively in Buffer B and Buffer B containing 0.1% NP40.
8. Add blocking buffer containing $^{125}$I-labeled SPA (approx. $5 \times 10^5$ cpm/ml). Shake for 45 minutes.
9. Wash once with Buffer B (10 minutes); four times with Buffer B containing 0.1% NP40 (10 minutes each wash); twice with Buffer B (10 minutes each wash).
10. Dry filters.
11. Expose to an x-ray film (Kodak X-Ray XAR-5) at −80° C. overnight or as needed.

Having now generally described the invention, the same will be further illustrated by means of specific examples which are presented herewith for purposes of illustration only and are not intended to be limiting thereof, unless otherwise specified.

EXAMPLES

Western Immunoblotting Detection of Denatured Apolipoproteins

Figure 6B:
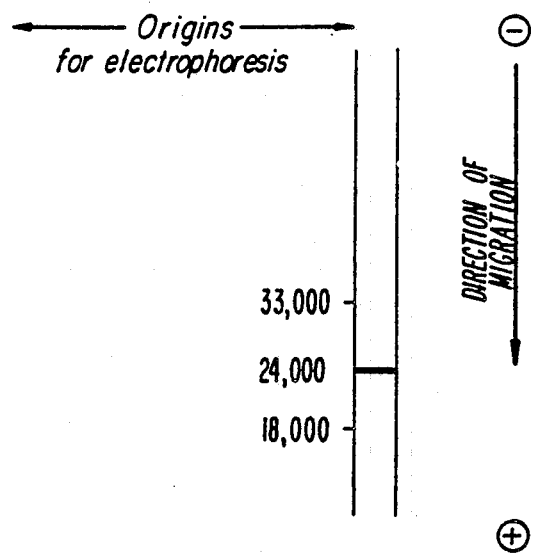

Electrophoretically-purified human apolipoproteins A-1, B and C-III ($C_3$) were purchased from Calbiochem-Behring, Inc. (LaJolla, California). Solutions containing 100 ug per ml of these proteins and a solution containing 100 ug/ml of purified human serum VLDL (as source of apolipoprotein E) were incubated in 1% sodium dodecyl sulfate (SDS) at 100° C. for 10 min. Samples with 1 ug apolipoprotein were applied to SDS-polyacrylamide gel (SDS-PAGE) and subjected to electrophoresis (SDS-PAGE) according to the procedure of Laemmli (*Nature*, 227: 680, 1970). The results are schematically represented in FIG. 6. In panel (A), lanes 1 and 2, a mixture of Apo-$A_1$ and Apo-$C_3$, was fractionated using a 13% SDS-PAGE. An 11% SDS-PAGE was used to fractionate Apo-E from 1 ug of VLDL applied in lane 3. A 5% SDS-PAGE was used to fractionate Apo-B applied in lane 4. The locations for molecular weight standards included in separate lanes for these gel systems is indicated between lanes 1 and 2 and lanes 3 and 4; the values given are in kilodaltons. After completion of electrophoresis, the Western technique described in "Specific Protocols IV" allowed for immunoblotting with specific peptide antisera using dilutions of 1:1000. Synthetic peptide antisera derived from peptides A' and B' from the Apo-$A_1$ peptides listed in FIG. 1 yielded the result shown in lane 1. Synthetic peptide antisera derived from the Apo-E peptide A' sequence listed in FIG. 2 yielded the result seen in lane 3. Synthetic peptide antisera derived from peptide A' from the Apo-$C_3$ sequence listed in FIG. 3 yielded the result shown in lane 2 and a similar result was obtained with antisera derived with peptide B' listed in FIG. 3. Synthetic peptide antisera from the Apo-B peptide A' shown in FIG. 4 yielded the result shown in lane 4. The positions for the bands indentified in each lane correspond to the known molecular weights for Apo-$A_1$ (24,000), Apo-B (200,000 to 500,000), Apo-E (33,000), and Apo-$C_3$ (12,000).

Our anti-peptide sera for Apo-B were derived from a sequence published by LeBoeuf, et al. (*FEBS Letters*, 170: 105, 1984) in which these investigators carried out partial N-terminal sequencing of an isolated, 24,000 MW and a 22,000 MW *Staphylococcus aureus* protease cleavage fragments of human Apo-B. In panel (B), approximately 5 ug of Apo-B was cleaved with *Staphylococcus aureus* protease and then subjected to gel electrophoresis through a 3 to 27% gradient SDS-PAGE. The Western immunoblot using the Apo-B peptide A' (FIG. 4) antisera detects a major band which binds the antibody at 24,000 MW as expected since the synthetic peptide originated from this protease fragment of Apo-B.

Example 2

Immunodot Blot Detection of Native Apolipoproteins

Immunodot blot analyses were performed using purified Apo-$A_1$, Apo-B and Apo-C III ($C_3$) to corroborate the specificity of the synthetic peptide antisera. This procedure was performed as described in "General Protocol III" and the autoradiographic results are schematically represented in FIG. 7. Strips of nitrocellulose filter paper were spotted with different quantities of Apo-B, Apo-$A_1$ or Apo-$C_3$ as indicated by the numbers, in micrograms, adjacent to each spot. A mixture of unrelated protein (1 ug per spot) was included on each filter strip and at the bottom of each strip, a mixture of the standards (1 ug) plus the indicated ug quantities of Apo-B, Apo-$A_1$ and Apo-$C_3$. Filter strips were subsequently incubated with synthetic peptide antisera (1:1000 dilution) and processed as described in "Protocol III." Strips are labeled from left to right Apo-B (with Apo-B spots and tested with antisera derived from peptide A' of FIG. 4; the same result was obtained, although not shown here, using antisera derived with peptide B' of FIG. 4), Apo-$A_1$ (with Apo-$A_1$ spots and tested with antisera derived from peptide A' of FIG. 1; the same result was obtained although not shown here, using antisera derived from peptide B' of FIG. 1), Apo-$C_3$ (with Apo-$C_3$ spots and tested with antisera derived from peptide A' of FIG. 3; the same result was obtained although not shown here using antisera derived from peptide B' of FIG. 3), and control (with Apo-$C_3$ spots and tested with antisera derived from peptide A' of FIG. 1; additional controls not shown using Apo-$A_1$ or Apo-B and peptide antisera derived from different apolipoproteins than the one spotted on the filter gave identical results, i.e. no binding of antibody and $^{125}$I-labeled protein A). The strip labeled VLDL was spotted with approximately 2, 1 and 0.5 ug quantities of purified human VLDL as well as with an unrelated protein mixture and VLDL added to the mixture indicated. Incubation with the peptide antisera (1:1000 dilution) derived from peptide A' from FIG. 2 resulted in specific detection of the Apo-E of VLDL as shown in this strip.

The same result as shown in FIG. 7, corroborating specificity of the synthetic peptide antisera, was obtained, although not shown here, using antisera derived from peptide C' of FIG. 1 (Apo-A), and from antisera derived from peptide C' of FIG. 3 (Apo-$C_3$), and from antisera derived from peptides A' and B' of FIG. 5 (Apo-$A_2$).

Example 3

ELISA Detection of Apolipoproteins

An analysis was performed using ELISA procedure as described in "Specific Protocol III" to corroborate the specificity of synthetic peptide antisera for human Apo-$A_2$. 50 ng per well of Apo-$A_2$ was used to demonstrate titers of 1:1600 and 1:800 for the following antibodies: (1) 50% ammonium sulfate precipitated and resuspended antibodies and (2) partially purified immunoglobulins from rabbits immunized according to "Specific Protocol II" with the Apo-$A_2$ peptides A' and B' of FIG. 5. Pre-immune and comparable fractions of sera from rabbits immunized with other synthetic peptides had negligible titers on the same Apo-$A_2$ antigen wells.

Example 4

Sandwich ELISA and Competition ELISA Detection of Apolipoproteins

Both a sandwich ELISA and a competition ELISA were developed using antibodies raised against certain synthetic apolipoprotein peptide fragments.

(a) In the sandwich ELISA, antibodies raised against synthetic peptides specific for Apo-$A_1$ were allowed to bind to ELISA wells in phosphate-buffered saline overnight. The wells were rinsed to remove unbound antibodies and subsequently incubated with serial dilutions of human serum which had either been de-lipidated (Chan, B. E. and Knowles, B. R., *J. Lipid Res.*, 17: 176-181 (1976)), treated with 4M guanidinehydrochloride or treated with 1% triton X100. After incubation at room temperature or 37° C. for one to two hours, the wells were rinsed extensively and then a commercially available Apo-$A_1$ monoclonal antibody diluted 1:500 was added. After one to two hours incubation, the wells were again rinsed and the specific binding of the murine monoclonal antibody was detected using horseradish peroxidase conjugated to rabbit anti-mouse IgG.

(b) In the competition ELISA, wells were coated with antibodies raised against synthetic peptides specific for Apo-$A_1$. The serum was diluted as in step (a) above. Serial dilutions of the serum were incubated in the wells with 5 to 15 nanograms of biotinylated Apo-$A_1$ protein (tracer) and the extent of competition for binding to the immobilized antibody was monitored after rinsing the wells using streptavidin-horseradish peroxidase conjugate binding followed by color formation.

Standard curves using sera with known concentrations of Apo-$A_1$ were generated for both assays (a) and (b) in order to quantitate the amounts of Apo-$A_1$ in test serums samples.

EXAMPLE 5

Antibodies raised against synthetic peptides specific for apolipoprotein $A_1$ were affinity purified and used to develop a single antibody (biotinylated) ELISA for serum testing.

Antisera containing the antibodies raised against the synthetic peptide A' of Apo-$A_1$ whose sequence is located near the $NH_2$ terminus of Apo-$A_1$, as shown in FIG. 1, was processed with affinity chromatography. The affinity column was prepared with the synthetic peptide and Sepharose. The specific antibody was eluted with 50 mM glycine at a pH of 2.5.

The peak fraction of eluted antibodies was shown by SDS-PAGE to consist predominantly of heavy and light chains from IgG, with a small amount of IgM heavy chains.

Having now fully described this invention, it will be apparent to one of ordinary skill in the art that the same may be carried out with minor modifications which do not affect the content or spirit thereof.

What is claimed is:

1. An immunogenic peptide fragment derivable from a naturally occurring amino acid sequence which is apolipoprotein type-specific, said peptide fragment selected from the group consisting of the following sequence:
   (a) Asp-Glu-Pro-Pro-Gln-Ser-Pro-Trp-Asp-Arg-Val-Lys-Asp
   (b) Arg-Thr-His-Leu-Ala-Pro-Tyr-Ser-Asp-Glu-Leu-Arg-Gln-Arg-Leu
   (c) Val-Lys-Ala-Lys-Val-Gln-Pro-Tyr-Leu-Asp-Asp-Phe
   (d) Ala-Val-Glu-Thr-Glu-Pro-Glu-Pro-Glu-Leu-Arg
   (e) Asp-Pro-Glu-Val-Arg-Pro-Thr-Ser-Ala-Val
   (f) Leu-Lys-Asp-Tyr-Trp-Ser-Thr-Val-Lys-Asp-Lys-Phe
   (g) Ser-Glu-Ala-Asp-Ala-Ser-Leu-Leu-Ser-Phe
   (h) Leu-Asp-Phe-Leu-Asn-Ile-Pro-Leu-Arg-Ile-Pro-Pro-Met-Arg
   (i) Ala-Lys-Pro-Ser-Val-Ser-Val-Glu-Phe-Val-Thr-Asn
   (j) Gln-Ala-Lys-Glu-Pro-Cys-Val-Glu-Ser-Leu and
   (k) Glu-Lys-Val-Lys-Ser-Pro-Glu-Leu-Gln-AlaGlu-Ala-Lys-Ser.

2. An immunogen comprising an immunogenic peptide fragment of claim 1 coupled to a carrier protein.

3. A peptide having the formula:

(1) $H_2N$—X—CO—$R^1$ 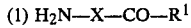

wherein
$R^1$ is Cys—CO—$R^2$, OH, OM or —$NR^3R^4$;
M is a pharmaceutically acceptable cation or a lower branched or unbranched alkyl group;
$R^2$, $R^3$ and $R^4$ are the same or different and selected from the group consisting of hydrogen and a lower branched or unbranched alkyl group; and
X is the peptide fragment selected from the group consisting of the following sequences:
   (a) Asp-Glu-Pro-Pro-Gln-Ser-Pro-Trp-Asp-Arg-Val-Lys-Asp
   (b) Arg-Thr-His-Leu-Ala-Pro-Tyr-Ser-Asp-Glu-Leu-Arg-Gln-Arg-Leu
   (c) Val-Lys-Ala-Lys-Val-Gln-Pro-Tyr-Leu-Asp-Asp-Phe
   (d) Ala-Val-Glu-Thr-Glu-Pro-Glu-Pro-Glu-Leu-Arg
   (e) Asp-Pro-Glu-Val-Arg-Pro-Thr-Ser-Ala-Val
   (f) Leu-Lys-Asp-Tyr-Trp-Ser-Thr-Val-Lys-Asp-Lys-Phe
   (g) Ser-Glu-Ala-Asp-Ala-Ser-Leu-Leu-Ser-Phe
   (h) Leu-Asp-Phe-Leu-Asn-Ile-Pro-Leu-Arg-Ile-Pro-Pro-Met-Arg
   (i) Ala-Lys-Pro-Ser-Val-Ser-Val-Glu-Phe-Val-Thr-Asn
   (j) Gln-Ala-Lys-Glu-Pro-Cys-Val-Glu-Ser-Leu and
   (k) Glu-Lys-Val-Lys-Ser-Pro-Glu-Leu-Gln-Ala-Glu-Ala-Lys-Ser;
(2) the acid addition salts thereof; and
(3) the protected or partially protected derivatives thereof.

4. A detectably labeled peptide fragment derivable from an amino acid sequence of claims 1 or 2 which is cross-reactive with apolipoprotein type-specific antibodies.

5. The detectably labeled peptide fragment of claim 4 wherein the detectable label is selected from the group consisting of a radiolabel, an enzyme label, a fluorescent label, a chemiluminescent label, and a bacteriophage label.

6. A method for detecting and/or quantitating ALP in a sample comprising:
   contacting said sample containing suspected ALP with a labeled peptide fragment according to claim 4 and an antibody to said ALP, and
   determining the extent of binding between said antibody and said labeled peptide fragment.

7. A kit for detecting ALP comprising a carrier means compartmentalized to receive one or more container means, at least one of said one or more container means containing a labeled peptide fragment according to claim 4.

8. Apolipoprotein type-specific antisera derivable by using a peptide fragment of any of claim 1, 2 or 3 as an immunogen.

9. Apolipoprotein type-specific detachably labeled antibody derived by using an immunogen comprising the peptide fragment of any of claims 1, 2 or 3.

10. A method for detecting and/or quantitating ALP in a sample comprising:
   contacting said sample suspected of containing ALP with a labeled antibody according to claim 9 and a second immobilized antibody which is cross-reactive with a domain on said ALP different than that with which said labeled antibody is cross-reactive and determining the amount of labeled antibody.

11. A kit for detecting ALP comprising a carrier means compartmentalized to receive one or more container means, at least one of said one or more container means containing labeled antibody according to claim 9, another of said one or more container means containing unlabeled antibody, said unlabeled antibody being specific to said ALP but cross-reacting with a different domain on said ALP.

* * * * *